(12) United States Patent
Hay et al.

(10) Patent No.: US 6,981,419 B1
(45) Date of Patent: Jan. 3, 2006

(54) PORTABLE DIRECT SENSOR ATTACHMENT SYSTEM

(76) Inventors: D. Robert Hay, 317H Rex Pl., Madeira Beach, FL (US) 33708-1938; Erling O. Nyborg, 1410 Kingsley Avenue, Dorval QC (CA) H9S 1G1

( * ) Notice: Subject to any disclaimer, the term of this patent is extended or adjusted under 35 U.S.C. 154(b) by 0 days.

(21) Appl. No.: 10/438,571

(22) Filed: May 15, 2003

(51) Int. Cl.
*G01N 29/04* (2006.01)
(52) U.S. Cl. ............................................. 73/636
(58) Field of Classification Search .......... 73/636, 73/639, 432.1, 866.5, 629, 659, 660, 736, 73/866; 367/120
See application file for complete search history.

(56) References Cited

U.S. PATENT DOCUMENTS

| | | | | | |
|---|---|---|---|---|---|
| 2,678,559 | A | * | 5/1954 | Drake | 73/636 |
| 2,958,818 | A | * | 11/1960 | Cowan et al. | 324/217 |
| 4,468,966 | A | * | 9/1984 | Bradshaw | 73/636 |
| 4,662,224 | A | * | 5/1987 | Turbe | 73/636 |
| 5,970,438 | A | * | 10/1999 | Clark et al. | 702/184 |

* cited by examiner

Primary Examiner—Hezron Williams
Assistant Examiner—Tamiko Bellamy
(74) Attorney, Agent, or Firm—Edward P. Dutkiewicz

(57) ABSTRACT

A vehicle equipped with monitoring equipment is adapted to ride a railroad track rail. An apparatus mount is coupled to the vehicle undercarriage. A downwardly displaced arm is coupled to the apparatus mount. A sensor mounting bracket couples a pair of railroad wheels and a pair of wheel bracket axles couples the wheels to the mounting bracket. A wheel axle couples one wheel to the arm. A sensor is positioned at a fixed adjustable distance above the top of the rail. The sensor is coupled to monitoring equipment with an electronic coupling means.

6 Claims, 4 Drawing Sheets

PORTABLE DIRECT SENSOR ATTACHMENT SYSTEM

BACKGROUND OF THE INVENTION

1. Field of the Invention

The present invention relates to a portable direct sensor attachment system and more particularly pertains to allowing a user to evaluate and detect flaws in railroad tracks.

2. Description of the Prior Art

The use of railroad track inspection systems is known in the prior art. More specifically, railroad track inspection systems previously devised and utilized for the purpose of detecting flaws in railroad tracks are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 6,262,572 issued Jul. 17, 2001, to Wojnarowski et al. discloses an electromagnetic system for railroad track crack detection and traction enhancement. U.S. Pat. No. 5,386,727 issued Feb. 7, 1995, to Earle discloses a dynamic rail longitudinal stress measuring system. Finally, U.S. Pat. No. 4,468,966 issued Sep. 4, 1984 to Bradshaw discloses a railroad track inspection car.

While these devices fulfill their respective, particular objectives and requirements, the aforementioned patents do not describe a portable direct sensor attachment system that allows allowing a user to evaluate and detect flaws in railroad tracks.

In this respect, the portable direct sensor attachment system according to the present invention substantially departs from the conventional concepts and designs of the prior art, and in doing so provides an apparatus primarily developed for the purpose of allowing a user to evaluate and detect flaws in railroad tracks.

Therefore, it can be appreciated that there exists a continuing need for a new and improved portable direct sensor attachment system which can be used for allowing a user to evaluate and detect flaws in railroad tracks. In this regard, the present invention substantially fulfills this need.

With greater specificity, the sensing devices, sensors, for the nondestructive testing of railroad rail and similar structures require that a sensor be placed and maintained in close proximity or in contact with the surface of the rail. These sensors must also be maintained in precise longitudinal and lateral alignment with respect to the rail to implement specific inspection procedures. The sensors or sensor carriage assembly is normally attached to the frame or body of a rail bound vehicle such as a highway/railway vehicle that can be driven along the rail. Alternatively, the sensors or sensor carriage may be assembled into an independent cart that is pulled along the rail by a rail-bound vehicle such as a locomotive or a highway/railway vehicle or carried between the wheels of such a vehicle.

In addition, means must be provided to ensure that the sensor or sensor carriage is protected from obstacles and anomalies in the rail surface geometries such as misalignment and gaps in the rail. When the sensor or the sensor carriage is attached to the frame of body of the host vehicle, the attachment mechanism must compensate for the vehicle suspension mechanisms and vehicle load conditions to provide the proximity, alignment and protection requirements of the sensors. When the sensor or sensor carriage is integrated into an independent cart that is pulled behind a rail-bound vehicle or carried between the wheels of the vehicle, the mechanism is bulky and complex. Size, weight and handling issues make placement and removal from the track and overall stability during movement over the rail.

In the method and apparatus of attachment of the present invention, the sensor or sensor carriage is attached directly to the wheels of the host vehicle that are used to guide the rail-bound vehicle on the rail thereby eliminating the effects of the suspension and related mechanism when attached to the chassis of the inspection vehicle or eliminating the need for an independent cart to be attached in some way to a rail-bound vehicle. The design facilitates rapid removal and egress or entrance of the inspection vehicle at any level crossing.

The present invention is a significant simplification over current rail inspection deployment mechanisms. Its simplicity makes the inspection capability portable and conveniently deployable on conventional rail maintenance and visual inspection vehicles that are in widespread use in railway systems and eliminates the need for costly suspension devices or special carts that are pulled behind or otherwise integrated into such vehicles. It is light in weight and can be removed easily from one vehicle and moved, carried by one person and mounted on another vehicle thereby readily providing an inspection capability on a fleet of vehicles.

In the case of electromagnetic acoustic transducers that must operate at a fixed minimum clearance above the rail surface, this device uses the magnetic force between the transducer and the rail to provide mechanical stability while facilitating precise setting of clearance distances as required.

This invention generally relates to nondestructive testing of railroad rails and further relates to an apparatus and method for maintaining a nondestructive testing sensor or array of sensors in close proximity or contact with the rail, in longitudinal and lateral alignment with the rail and follows the anomalies in the vertical rail surface profile to protect the sensor(s) from damage from such anomalies.

High reliability is essential in the operation of a railroad system to assure the safety of the public and passengers and the safe and efficient movement of goods. U.S. railways carry high and increasingly higher freight tonnages. A key high-performance element in the system is the rail. These operational factors in diverse climatic environments present several challenges to rail integrity. As a load-bearing component, rail requires a high level of materials integrity that depends on quality control of rail manufacturing and in-service inspection of rail. Over the decades of experience with inspection of rail for internal defects both ultrasonics and magnetic flux leakage have been used. Of these, ultrasonics has become the method of choice because it generates more information than magnetic flux leakage about a wider range of defects.

The ultrasonic or magnetic flux leakages or other sensor is carried on a host vehicle and is generally attached to the frame of body of the host vehicle through a carriage mechanism designed to maintain proximity or contact with the rail, alignment and protection from rail surface anomalies. In these current configurations, the attachment mechanism between the vehicle chassis and the rail is complex because it has to follow not only the rail but also the vehicle movements through the suspension system. The behavior of the vehicle chassis is not consistent and depends on such factors as the vehicle payload and its distribution. These compensations are provided through devices such as pantograph assemblies and mechanisms such as pneumatic and hydraulic as well as spring actuators and mechanical guide devices to provide the required positioning and protection.

They are mounted on specialized vehicles, trailer assemblies or other complex mechanisms for rail inspection. This results in costly mechanisms and costly inspections with attendant low availability of inspection systems and lower frequency of inspection than would be desirable to maintain rail system reliability.

There is a need for a simpler mechanism to lower the cost of inspection equipment, to lower the cost of inspection and provide more frequent and reliable inspection. This requirement applies to conventional ultrasonic testing and other methods used for nondestructive testing of rail but are particularly required with the use of electromagnetic acoustic transducers used to introduce ultrasonic waves. In this case, it may be required to maintain a certain lift-off between the sensor and the rail.

SUMMARY OF THE INVENTION

In view of the foregoing disadvantages inherent in the known types of railroad track inspection systems now present in the prior art, the present invention provides an improved portable direct sensor attachment system. As such, the general purpose of the present invention, which will be described subsequently in greater detail, is to provide a new and improved portable direct sensor attachment system and method which has all the advantages of the prior art and none of the disadvantages.

To attain this, the present invention essentially comprises a vehicle. The vehicle is equipped with monitoring equipment. The vehicle has an undercarriage. The vehicle is adapted to ride along a railroad track rail.

An apparatus mount is provided. The apparatus mount is coupled to the vehicle undercarriage. A mounting pin aperture is provided through the apparatus mount.

A downwardly displaced arm is provided next. The downwardly displaced arm has an upper end and a lower end. A centrally located mounting pin aperture is provided through the upper end. A wheel axle hole is provided through the lower end.

Next provided is a mounting pin. The mounting pin is fabricated of rigid material. The mounting pin pivotably couples the downwardly displaced arm and the apparatus mount.

A pair of railroad wheels is provided. Each railroad wheel has a inner side and an outer side. A thickness is provided between the inner side and the outer side. The inner side of the first wheel has a flange of a first diameter. In this manner the wheel is secured on a railroad track rail. The outer side has a round track contact surface of a second diameter. The second wheel has a second diameter. Each of the wheels has a plurality of radially located studs.

Provided next is a first wheel axle. The first wheel axle is fabricated of rigid material. The first wheel axle couples the first railroad wheel to the downwardly displaced arm.

A sensor mounting bracket has an inside and an outside. A thickness is provided between the inside and the outside. The sensor mounting bracket has an inward end and an outward end. An extent is provided between the inward end and the outward end. The bracket has a first wheel axle aperture on the inward end. In this manner the bracket may be coupled to the first rail wheel. A second wheel axle aperture is provided on the outward end of the wheel. In this manner the bracket is coupled to the second rail wheel. The bracket has a plurality of bolt holes. The bolt holes are centrally located on the extent of the bracket.

Provided next is a first wheel bracket axle. The first wheel bracket axle is fabricated of rigid material to couple the first wheel to the mounting bracket.

A second wheel bracket axle is provided. The second wheel bracket axle is fabricated of rigid material to couple the second railroad wheel to the mounting sensor bracket.

A downwardly displaced L-shaped attachment member is provided next. A plurality of slots is provided through the downwardly displaced L-shaped attachment member. In this manner the downwardly displaced L-shaped attachment member is coupled to the mounting bracket and the attachment member.

Further provided is a sensor. The sensor is from the class that includes piezoelectric, electromagnetic, electromagnetic-acoustic, air-coupled and laser-ultrasonic phased array sensors. The sensor is coupled to the sensor mounting bracket. The sensor is located between the first and second wheel. The sensor is maintained in a fixed but adjustable position ranging from contact to about $3/4$ inches above the top of a railroad track rail for electromagnetic-acoustic and higher for air-coupled and laser transduction.

Provided last is an electronic coupling means, such as wire. In this manner the sensor is coupled to the monitoring equipment.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved portable direct sensor attachment system which has all of the advantages of the prior art railroad track inspection systems and none of the disadvantages.

It is another object of the present invention to provide a new and improved portable direct sensor attachment system which may be easily and efficiently manufactured and marketed.

It is further an object of the present invention to provide a new and improved portable direct sensor attachment system which is of durable and reliable construction.

An even further object of the present invention is to provide a new and improved portable direct sensor attachment system which is susceptible of a low cost of manufacture with regard to both materials and labor, and which accordingly is then susceptible of low prices of sale, thereby making such portable direct sensor attachment system economically available.

Even still another object of the present invention is to provide a portable direct sensor attachment system for allowing a user to evaluate and detect flaws in railroad tracks.

Lastly, it is an object of the present invention to provide a new and improved portable direct sensor attachment system. A vehicle equipped with monitoring equipment is adapted to ride a railroad track rail. An apparatus mount is coupled to the vehicle undercarriage. A downwardly displaced arm is coupled to the apparatus mount. A sensor mounting bracket couples a pair of railroad wheels and a pair of wheel bracket axles couples the wheels to the mounting bracket. A wheel axle couples one wheel to the arm. A sensor is positioned between the wheels and is maintained in a fixed but adjustable position ranging from contact to about ¾ inches above the top of the rail for electromagnetic-acoustic and higher for air-coupled and laser transduction. The sensor is coupled to monitoring equipment with an electronic coupling means.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
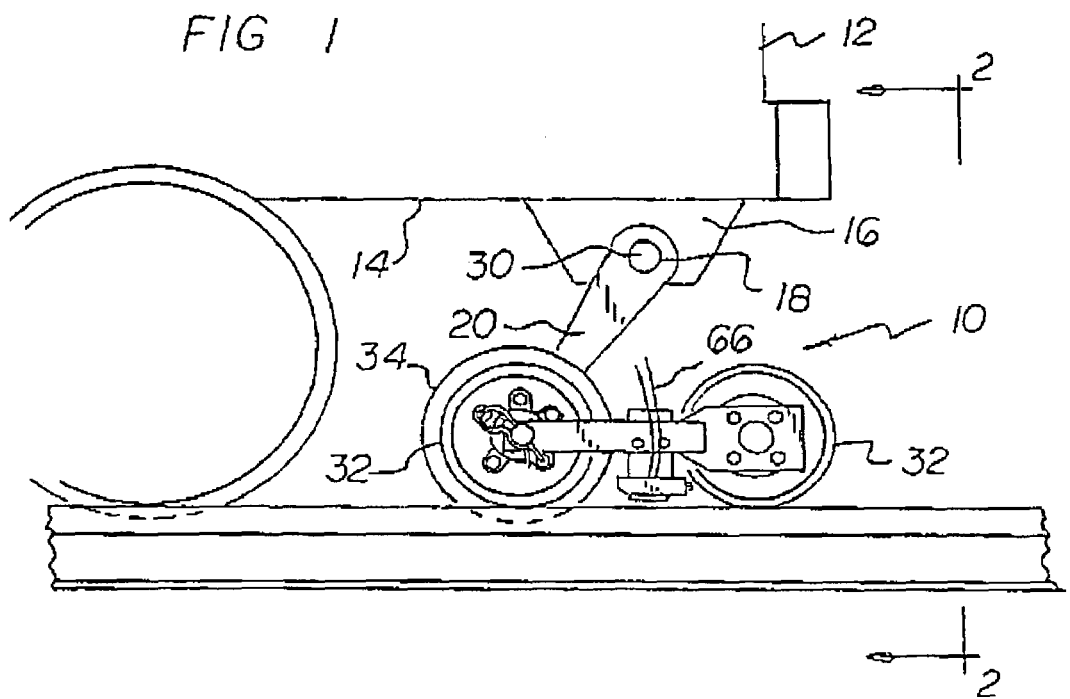
FIG. 1 is a side elevational view of a portable direct sensor attachment system constructed in accordance with the principles of the present invention.
Figure 2:
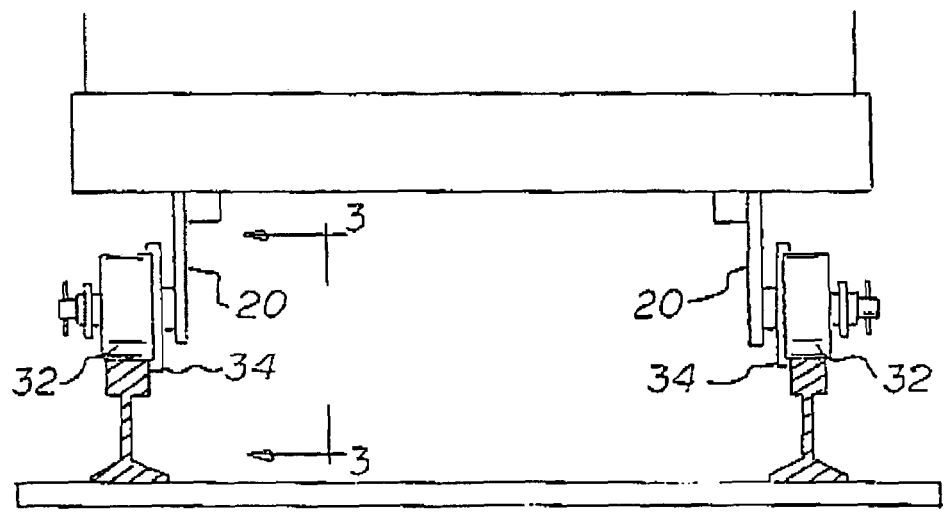
FIG. 2 is a front elevational view taken along line 2—2 of FIG. 1.
Figure 3:
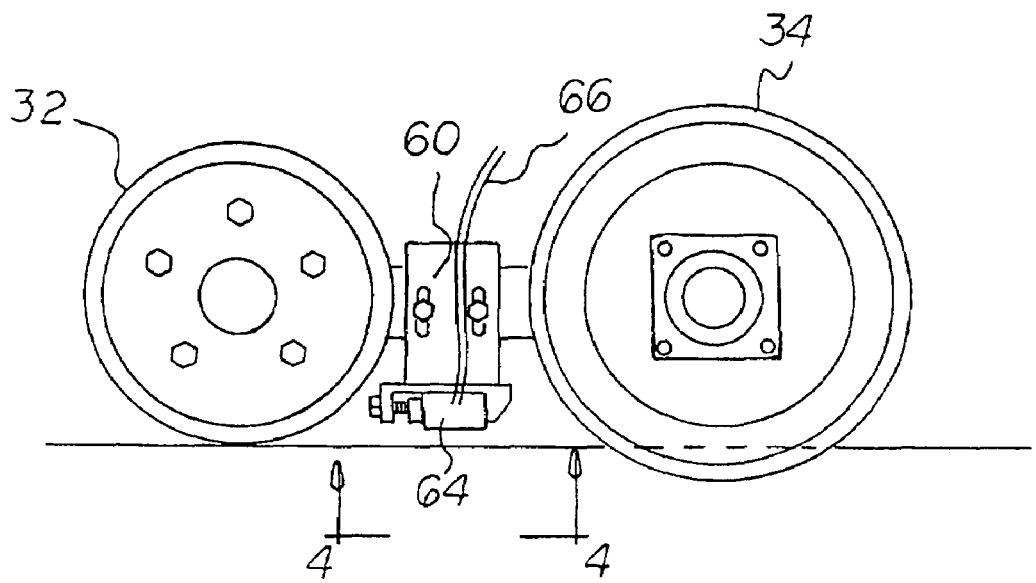
FIG. 3 is a side elevatonal view taken along line 3—3 of FIG. 2.
Figure 4:
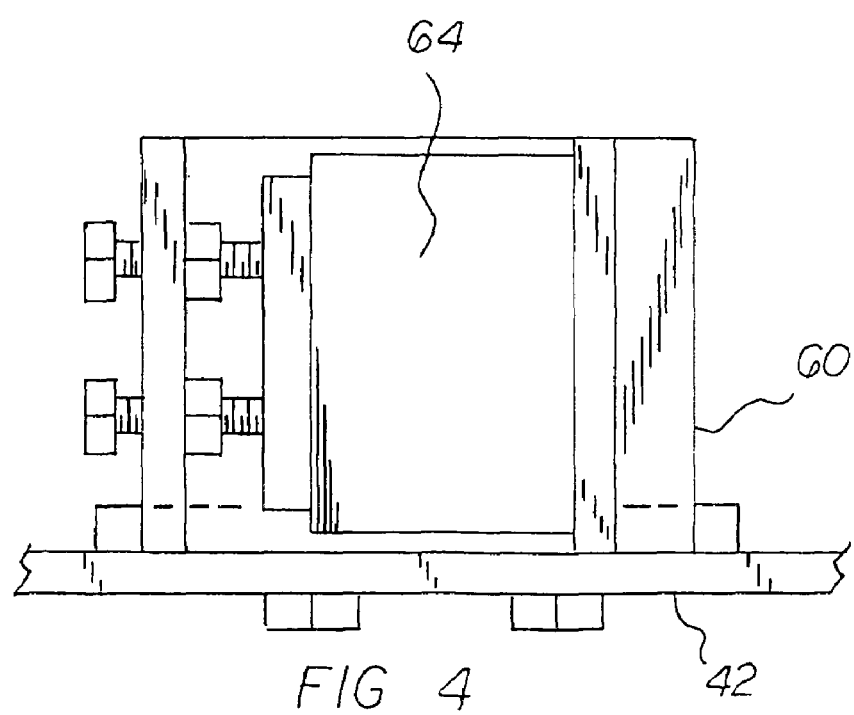
FIG. 4 is a bottom view taken along line 4—4 of FIG. 3.
Figure 5:
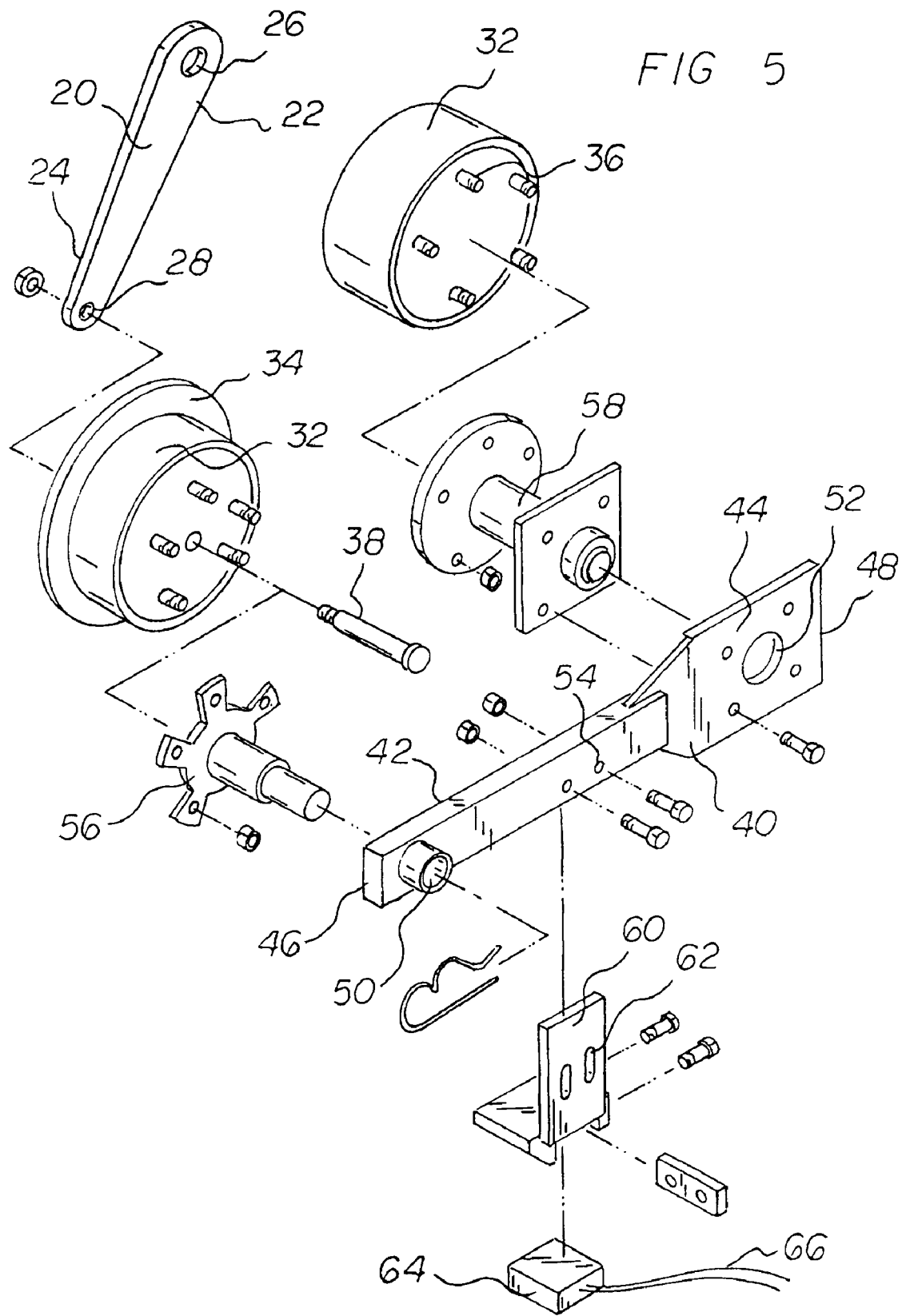
FIG. 5 is an exploded perspective view of the system of the prior Figures.

With reference now to the drawings, and in particular to FIG. 1 thereof, the preferred embodiment of the new and improved portable direct sensor attachment system embodying the principles and concepts of the present invention and generally designated by the reference numeral 10 will be described.

The present invention, the portable direct sensor attachment system 10 is comprised of a plurality of components. Such components in their broadest context include a vehicle, an apparatus mount, a downwardly displaced arm, a pair of railroad wheels, a wheel axle, a sensor mounting bracket, a sensor, and an electronic coupling means. Such components are individually configured and correlated with respect to each other so as to attain the desired objective.

First provided is a vehicle 12. The vehicle is equipped with monitoring equipment. The vehicle has an undercarriage 14. The vehicle is adapted to ride along a railroad track rail.

An apparatus mount 16 is provided. The apparatus mount is coupled to the vehicle undercarriage. A mounting pin aperture 18 is provided through the apparatus mount.

A downwardly displaced arm 20 is provided next. The downwardly displaced arm has an upper end 22 and a lower end 24. A centrally located mounting pin aperture 26 is provided through the upper end. A wheel axle hole 28 is provided through the lower end.

Next provided is a mounting pin 30. The mounting pin is fabricated of rigid material. The mounting pin pivotably couples the downwardly displaced arm and the apparatus mount.

A pair of railroad wheels 32 is provided. Each railroad wheel has an inner side and an outer side. A thickness is provided between the inner side and the outer side. The inner side of the first wheel has a flange 34 of a first diameter. In this manner the vehicle is secured on a railroad track rail. The outer side has a round track contact surface of a second diameter. The second wheel has a second or other diameter. Each of the wheels has a plurality of radially located studs 36.

Provided next is a first wheel axle 38. The first wheel axle is fabricated of rigid material. The first wheel axle couples the first railroad wheel to the downwardly displaced arm.

A sensor mounting bracket 40 has an inside 42 and an outside 44. A thickness is provided between the inside and the outside. The sensor mounting bracket has an inward end 46 and an outward end 48. An extent is provided between the inward end and the outward end. The bracket has a first wheel axle aperture 50 on the inward end. In this manner the bracket may be coupled to the first rail wheel. A second wheel axle aperture 52 is provided on the outward end of the wheel. The aperture 50 is equipped with a bushing or appropriate bearing so that it easily slides over the wheel axle 56. In this manner the bracket is coupled to the second rail wheel. The bracket has a plurality of bolt holes 54. The bolt holes are centrally located on the extent of the bracket.

Provided next is a first wheel bracket axle 56. The first wheel bracket axle is fabricated of rigid material to couple the first wheel to the mounting bracket.

A second wheel bracket axle 58 is provided. The second wheel bracket axle is fabricated of rigid material to couple the second railroad wheel to the mounting sensor bracket.

A downwardly displaced L-shaped attachment member 60 is provided next. A plurality of slots 62 is provided through the downwardly displaced L-shaped attachment member. In this manner the downwardly displaced L-shaped attachment member is coupled to the mounting bracket and the attachment member.

Further provided is a sensor 64. The sensor is from the class that includes piezoelectric, electromagnetic, electromagnetic-acoustic, air-coupled and laser-ultrasonic phased array sensors. The sensor is coupled to the sensor mounting bracket. The sensor is located between the first and second wheel. The sensor is maintained in a fixed but adjustable position ranging from contact to about ¾ inches above the top of the railroad track rail for electromagnetic-acoustic and higher for air-coupled and laser transduction.

Provided last is an electronic coupling means 66, such as wire. In this manner the sensor is coupled to the monitoring equipment.

This invention involves a simple sensor attachment mechanism that is attached directly to a guide wheel that is in direct contact with the rail and eliminates the requirement for a complex, adaptive mechanism between the host vehicle chassis and the rail. By maintaining close proximity to the guide wheel, the sensor tracks the lateral and vertical positions without the need for suspension mechanisms.

There are two generic embodiments of the invention: 1) rail conversion gear guide wheels on highway/railway vehicles, and 2) wheels on dedicated rail vehicles. It can also be attached to the structure that is directly attached to the wheel, such as on arm 20.

In the primary embodiment (FIG. 1) a wheel plate is attached to the guide wheel of the rail vehicle. The wheel plate consists of a flange with holes in the same positions as the bolts that hold the vehicle guide wheel to its hub. These same bolts attach the wheel plate to the vehicle guide wheel. This flange has an axle attached that is concentric with the axis of rotation of the vehicle guide wheel. This wheel plate with concentric axle is attached to the vehicle guide wheel using simple tools. The portable sensor carriage is attached by sliding bushing equipped aperture 50 onto the wheel axle 56 and pinning the sensor carriage assembly in place on the axle. The figures show the carriage assembly consisting of the support arm and rear wheel attached and pinned to the vehicle guide wheel axle. In this primary embodiment, the vehicle guide wheel used for attachment can be the guide wheel on a highway/railway conversion assembly or the wheel on any rail bound vehicle. The wheel plate design is adapted to accommodate the details of the specific guide wheel available on the vehicle.

In a variation on the primary embodiment, a fixed axle for supporting the sensor carriage assembly is attached to the inside of the vehicle arm 20, centered on the axle hole 28 and parallel to and concentric with the mounting pin 30. Because the sensor carriage assembly is supported on the track, at its outward end by a wheel (or other contact device) and pivots about the center of the vehicle guide wheel, the primary embodiment in both of its variations provides precise and accurate positioning of the sensor above the track. This embodiment is capable of maintaining the clearance distances required for electromagnetic sensors (of the order of 1/64 inch) and simultaneously overcoming the large attractive forces between the electromagnetic sensor and the rail.

Figure 6:
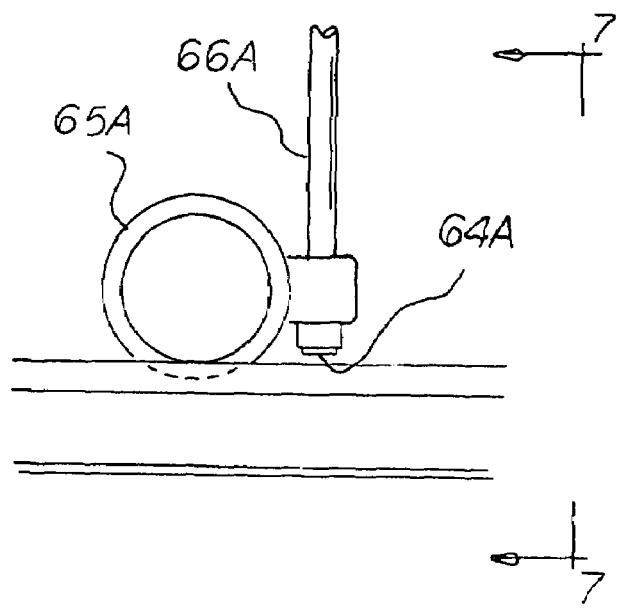
FIGS. 6 and 7 are side and front views of the system of an alternate embodiment of the invention.
Figure 7:
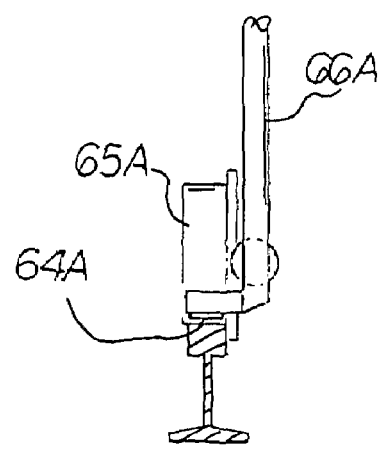

In the secondary embodiment the vehicle guide wheel has a vertical post supporting the vehicle. The drawings show the vertical support post in two configurations, one centered on the vehicle guide wheel and the other offset from the guide wheel. In either configuration the sensor attaches to an arm or bracket that is attached to the vehicle guide wheel. In the embodiment of FIGS. 6 and 7, as well as FIGS. 8 and 9, the attachment fixture can be the part of a highway/railway conversion assembly or any fixture that is attached directly to the wheel or a rail bound vehicle prior to any suspension, damping or other position compensating device or component between the guiding wheel and the vehicle frame or chassis.

Figure 8:
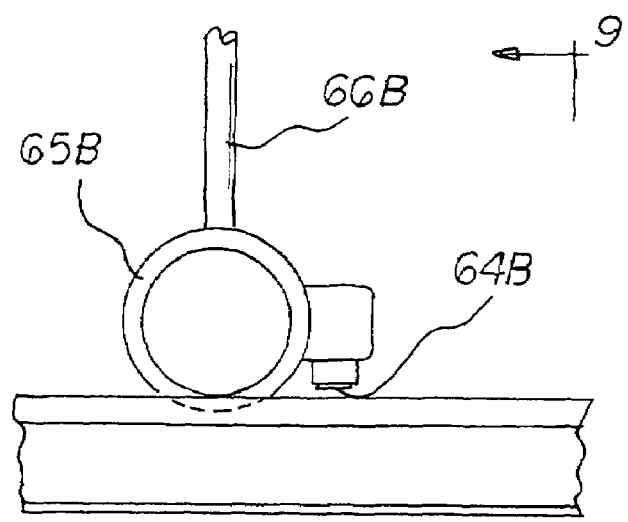
FIGS. 8 and 9 are side and front views of the system of another alternative embodiment of the invention.
Figure 9:
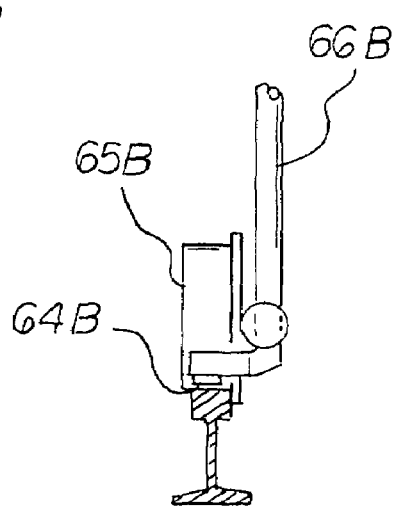

In the embodiment of FIGS. 6 and 7, the sensor carriage assembly 64A is radially offset from the guide wheel 65A with the rod 66A to the vehicle frame or chassis being laterally offset form the guide wheel. In the embodiment of FIGS. 8 and 9, the sensor carriage assembly 64B is radially offset from the guide wheel 65B with the rod 66B to the vehicle frame or chassis being aligned with the vertical diameter of the guide wheel.

This invention can be used to carry any type of sensors and sensor assemblies over the rail including piezoelectric, electromagnetic, electromagnetic-acoustic, air-coupled, laser ultrasonic phased-arrays and other means of introducing ultrasonic waves and electromagnetic fields and detecting ultrasonic waves and electromagnetic fields in rail to detect defects and to measure residual and longitudinal stress. This includes single, multi-purpose sensors as well as multiple transducer assemblies. For example, it is clearly contemplated by the invention that a pair of ultrasonic sensors can be used for transmission and detection functions. It also includes contact and non-contact transduction methods.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A portable direct sensor attachment system for allowing a user to evaluate and detect flaws in railroad tracks comprising, in combination:

a vehicle equipped with monitoring equipment having an undercarriage that adapts the vehicle to ride along a railroad track rail;

an apparatus mount coupled to a first rail wheel on the undercarriage, the apparatus mount having a mounting pin aperture there through;

a downwardly displaced arm having an upper end and a lower end, the upper end having a centrally located mounting pin aperture there through with the lower end having a wheel axle hole there through;

a mounting pin fabricated of rigid material and pivotably coupling the downwardly displaced arm and the apparatus mount;

a pair of railroad vehicle wheels each having an inner side and an outer side and a thickness there between, the inner side of the first wheel having a flange of a first diameter to secure the vehicle on a railroad track rail and the outer side having a round track contact surface of a second diameter, the second wheel having a second diameter, with each of the wheels having a plurality of radially located studs;

a first wheel axle fabricated of rigid material to couple the first railroad wheel to the downwardly displaced arm;

a sensor mounting bracket having an inner side and an outer side and a thickness there between, and an inward end and an outward end with an extent there between, the bracket having a first wheel axle aperture on the inward end to allow coupling the bracket to the vehicle wheel, the bracket having a second wheel axle aperture on the outward end to allow coupling of the bracket to the second rail wheel, the bracket having a plurality of bolt holes centrally located on the extent of the bracket;

a first wheel bracket axle fabricated of rigid material to couple the first railroad wheel to the mounting sensor bracket;

a second wheel bracket axle fabricated of rigid material to couple the second railroad wheel to the mounting sensor bracket;

a sensor being one of the sensors from the class that includes piezoelectric, electromagnetic, electromagnetic-acoustic, air-coupled and laser-ultrasonic phased array sensors, the sensor being coupled to the sensor mounting bracket and being located between the first and second wheel, the sensor being maintained at a fixed height above the top of a railroad track rail with mechanisms for adjusting the fixed height for electromagnetic-acoustic, air coupled and laser transduction sensors; and an electronic coupling means for coupling the sensor to monitoring equipment.

2. A portable direct sensor attachment system comprising, in combination:
   a vehicle equipped with monitoring equipment adapted to ride a rail;
   an apparatus mount coupled to the vehicle undercarriage,
   a downwardly displaced arm coupled to the apparatus mount;
   a pair of railroad wheels;
   a wheel axle to couple one wheel to the arm;
   a sensor mounting bracket coupling the two wheels;
   a pair of wheel bracket axles to couple the wheels to the sensor mounting bracket;
   a sensor attached to the sensor mounting bracket at a fixed adjustable distance above the top of a railroad track rail independent of the movement of the vehicle; and
   an electronic coupling means for coupling the sensor to monitoring equipment.

3. A portable direct sensor attachment system as described in claim 2 wherein the sensor sends and reads signals in a plurality of directions.

4. A portable direct sensor attachment system as described in claim 2 wherein the electronic coupling means used for coupling the sensor is a radio frequency signal.

5. A device and attachment means for positioning sensors used for nondestructive testing of rail that enables the sensor to maintain alignment and to maintain a precise but adjustable clearance above the rail surface, for electromagnetic-acoustic, air-coupled and laser transduction sensors and to follow directly and to compensate for the anomalies in the rail surface comprising:
   a bushing or bearing assembly that attaches directly to a vehicle wheel guide or a rail gear conversion system that is used to convert a highway vehicle to rail operation, the attachment made to the rotational axis of whatever vehicle wheel is used to contact the rail and to guide the vehicle on the rail;
   a bracket that attaches to the bushing or bearing assembly to a second independent wheel or track contact device and carries the sensor carriage assembly; and
   a sensor carriage assembly that contains one or more sensors the sensor carriage assembly being attached to the bracket and radially offset from the guide wheel with the rod to the vehicle frame or chassis being laterally offset from the guide wheel.

6. A device and attachment means for positioning sensors used for nondestructive testing of rail that enables the sensor to maintain alignment and to maintain a precise but adjustable clearance above the rail surface, for a range of desired clearances not greater than about ¾ inches for an electromagnetic-acoustic sensor and higher for air-coupled and laser transduction sensors and to follow directly and to compensate for the anomalies in the rail surface comprising:
   a bearing assembly that attaches directly to a wheel guide of a rail gear conversion system that is used to convert a highway vehicle to rail operation, the attachment made to the rotational axis of whatever vehicle wheel is used to contact the rail and to guide the vehicle on the rail; a bracket that attaches the bearing assembly to a second independent wheel that carries a sensor carriage assembly;
   wherein the sensor carriage assembly contains the rail defect sensors and wherein the sensor carriage assembly is attached to the bracket and radially offset from the guide wheel with the rod to the vehicle frame or chassis being aligned with the vertical diameter of the guide wheel.

* * * * *